United States Patent [19]

Walker

[11] 4,277,486
[45] * Jul. 7, 1981

[54] 1-[(SUBSTITUTED-NAPHTHYL)ETHYL]-IMIDAZOLE DERIVATIVES

[75] Inventor: Keith A. M. Walker, Los Altos Hills, Calif.

[73] Assignee: Syntex (U.S.A.) Inc., Palo Alto, Calif.

[*] Notice: The portion of the term of this patent subsequent to Apr. 17, 1996, has been disclaimed.

[21] Appl. No.: 19,202

[22] Filed: Mar. 9, 1979

[51] Int. Cl.$^3$ .................. A61K 31/415; C07D 233/60; C07D 405/06

[52] U.S. Cl. .................. 424/273 R; 548/336; 548/341

[58] Field of Search ............... 548/341, 336; 424/273 R

[56] References Cited

U.S. PATENT DOCUMENTS

| | | | |
|---|---|---|---|
| 4,085,209 | 4/1978 | Miller et al. | 548/341 |
| 4,141,908 | 2/1979 | Heeres | 548/336 |
| 4,150,153 | 4/1979 | Walker | 548/341 |
| 4,156,008 | 5/1979 | Heeres | 548/336 |
| 4,172,141 | 10/1979 | Walker | 548/341 |

Primary Examiner—Henry R. Jiles
Assistant Examiner—Natalia Harkaway
Attorney, Agent, or Firm—Annette M. Moore; Tom M. Moran; Alan M. Krubiner

[57] ABSTRACT

Compounds of the formula

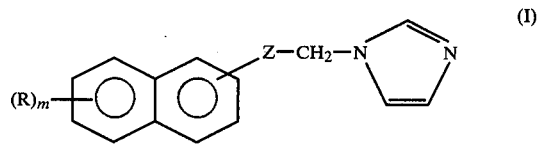

(I)

wherein m is the integer 1, 2 or 3; R is independently selected from the group $C_1$ to $C_6$ alkyl, $C_1$ to $C_6$ alkoxy, halo, trifluoromethyl and hydroxy when m is the integer 1, 2 or 3 and methylenedioxy when m is the integer 2; Z is hydroxymethylene, esterified hydroxymethylene, alkoxymethylene, alkylthiomethylene, carbonyl, or ketal-, thioketal- or hemithioketal- protected carbonyl, and the pharmaceutically acceptable acid addition salts thereof, are useful as anticonvulsants, antisecretory agents and spermatocides.

8 Claims, No Drawings

1-[(SUBSTITUTED-NAPHTHYL)ETHYL]-IMIDAZOLE DERIVATIVES

The present invention relates to certain 1-[(substituted-naphthyl)ethyl]imidazole derivatives. More particularly, the present invention relates to compounds of formula (I), namely:

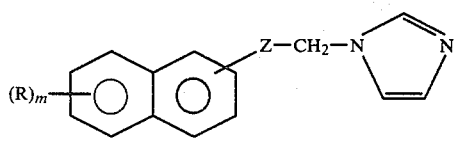

wherein m is the integer 1, 2 or 3; R is independently selected from the group $C_1$ to $C_6$ alkyl, $C_1$ to $C_6$ alkoxy, halo, trifluoromethyl and hydroxy when m is the integer 1, 2 or 3 and methylenedioxy when m is the integer 2; Z is hydroxymethylene, esterified hydroxymethylene, alkoxymethylene, alkylthiomethylene, carbonyl, or ketal-, thioketal- or hemithioketal-protected carbonyl; and the pharmaceutically acceptable acid addition salts thereof.

Compounds of formula (I) exhibit a broad spectrum of CNS related activity such as anticonvulsant activity (as demonstrated by the maximal electroshock seizure test), anorexigenic, antidepressant and muscle relaxing activity; as well as inhibition of gastric secretion, antihypertensive, spermatocidal and spermatostatic activities.

One aspect of the present invention relates to a method for treating and/or preventing convulsions in a mammalian subject comprising administering a therapeutically effective amount of a compound of formula (I), or a pharmaceutically acceptable acid addition salt thereof. Another aspect of the present invention relates to pharmaceutical compositions useful for the treatment and/or prevention of convulsions in a mammalian subject comprising a compound of formula (I), or a pharmaceutically acceptable acid addition salt thereof, in admixture with a pharmaceutically acceptable non-toxic carrier. For this utility compounds of formula (I) wherein Z is carbonyl, ketal-protected carbonyl or alkoxymethylene are particularly preferred.

Yet another aspect of the present invention relates to a method for inhibiting gastric secretion in a mammalian subject comprising administering a therapeutically effective amount of a compound of formula (I), or a pharmaceutically acceptable acid addition salt thereof. Still another aspect of the present invention relates to pharmaceutical compositions useful for the inhibition of gastric secretion in a mammalian subject comprising a compound of formula (I), or a pharmaceutically acceptable acid addition salt thereof, in admixture with a pharmaceutically acceptable non-toxic carrier. For this utility compounds of formula (I) wherein Z is thioketal-protected carbonyl are particularly preferred.

A further aspect of the present invention concerns a process for the preparation of a free base compound of the formula

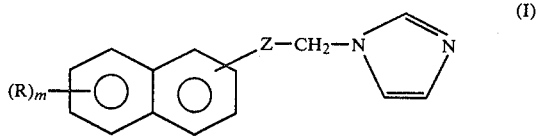

wherein m is the integer 1, 2 or 3; R is independently selected from the group $C_1$ to $C_6$ alkyl, $C_1$ to $C_6$ alkoxy, halo, trifluoromethyl and hydroxy when m is the integer 1, 2 or 3 and methylenedioxy when m is the integer 2; Z is hydroxymethylene, esterified hydroxymethylene, alkoxymethylene, alkylthiomethylene, carbonyl, or ketal-, hemithioketal- or thioketal-protected carbonyl; or a pharmaceutically acceptable non-toxic acid addition salt thereof, which process comprises:

(a) the preparation of a compound of formula (I) wherein Z is carbonyl by reaction of a halomethyl naphthyl ketone with imidazole, or (b) the preparation of a compound of formula (I) wherein Z is hydroxymethylene by reduction of a compound of formula (I) wherein Z is carbonyl, or (c) the preparation of a compound of formula (I) wherein Z is esterified hydroxymethylene by esterification of a compound of formula (I) wherein Z is hydroxymethylene, or (d) the preparation of a compound of formula (I) wherein Z is ketal protected carbonyl by ketalization of a compound of formula (I) wherein Z is carbonyl, or (e) the preparation of a compound of formula (I) wherein Z is hemithioketal-protected carbonyl by hemithioketalization of a compound of formula (I) wherein Z is carbonyl, or (f) the preparation of a compound of formula (I) wherein Z is thioketal-protected carbonyl by thioketalization of a compound of formula (I) wherein Z is carbonyl, or (g) the preparation of a compound of formula (I) wherein Z is ketal-protected carbonyl by reaction of a compound of the formula

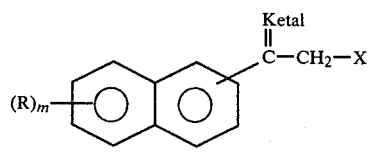

wherein X is halo, with an alkali metal salt of imidazole, or (h) the preparation of a compound of formula (I) wherein Z is hydroxymethylene by reaction of a compound of the formula

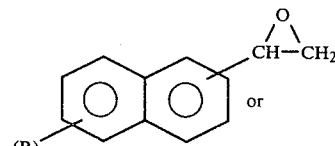

or

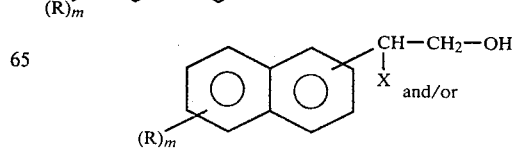

and/or

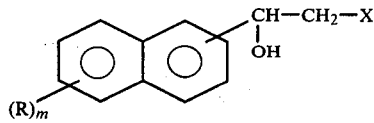

with imidazole and/or an alkali metal salt thereof, or (i) the preparation of a compound of formula (I) wherein Z is alkoxymethylene by alkylation of a compound of formula (I) wherein Z is hydroxymethylene, or (j) the preparation of a compound of formula (I) wherein Z is alkylthiomethylene by conversion of a compound of formula (I) wherein Z is hydroxymethylene to a reactive ester (e.g. halide or sulfonate) followed by reaction with an alkylthiol, or (k) optionally converting a free base to the corresponding acid addition salt, or (l) optionally converting an acid addition salt to the corresponding free base.

The compounds of the present invention are represented by the formula

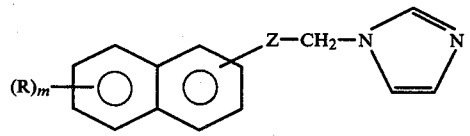

wherein m is the integer 1, 2 or 3; R is independently selected from the group $C_1$ to $C_6$ alkyl, $C_1$ to $C_6$ alkoxy, halo, trifluoromethyl and hydroxy when m is the integer 1, 2 or 3 and methylenedioxy when m is the integer 2; Z is hydroxymethylene, esterified hydroxymethylene, alkoxymethylene, alkylthiomethylene, carbonyl, or a ketal-, thioketal- or hemithioketal-protected carbonyl; and the pharmaceutically acceptable acid addition salts thereof.

Included in the compounds of formula I are the following subgeneric compounds:

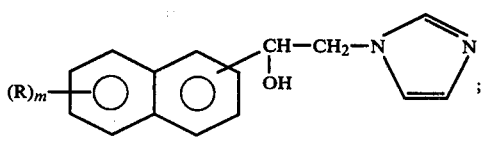

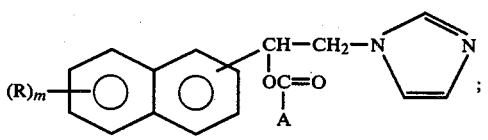

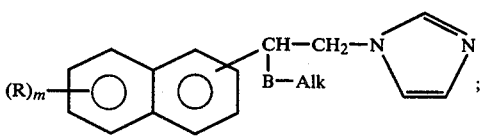

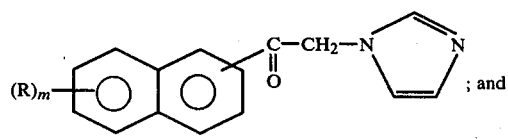
; and

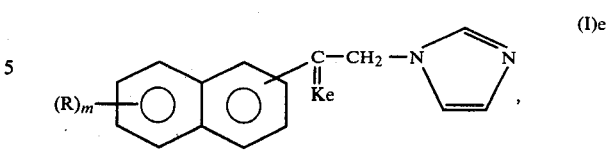

where m is the integer 1, 2 or 3; R is independently selected from the group $C_1$ to $C_6$ alkyl, $C_1$ to $C_6$ alkoxy, halo, trifluoromethyl and hydroxy when m is the integer 1, 2 or 3 and methylenedioxy when m is the integer 2; B is oxygen or sulfur; Alk is $C_1$ to $C_6$ alkyl; A is hydrogen, $C_1$ to $C_5$ alkyl, or phenyl optionally substituted with one to three substituents independently selected from $C_1$ to $C_6$ alkyl, $C_1$ to $C_6$ alkoxy and halo; Ke is selected from the group ketal-protected carbonyl, thioketal-protected carbonyl and hemithioketal-protected carbonyl; and the pharmaceutically acceptable acid addition salts thereof.

Of the above subgeneric compounds of formula (I), the compounds preferred are those selected from the group (I)a, (I)b, (I)c, (I)d and (I)e selected from the group ketal-protected carbonyl and thioketal-protected carbonyl.

In the preferred compounds of formula (I)c it is particularly preferred that the group Alk is $C_1$ to $C_3$ alkyl, most preferably methyl.

In the preferred compounds of formula (I)e it is particularly preferred that the group Ke is ketal-protected carbonyl, most preferably derived from ethylene glycol.

Of the above preferred, particularly preferred and most preferred compounds it is further particularly preferred that R is selected from the group $C_1$ to $C_4$ alkyl and halo, most preferably methyl, ethyl, chloro or bromo preferably with m the integer 1 or 2 most preferably the integer 1. In these preferred, particularly preferred and most preferred compounds, when the side chain

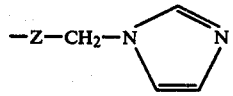

is attached to the 1-position of the naphthalene nucleus, it is preferred that the group R is attached at the 4- or 7-position when m is the integer 1 or at the 2,3-; 2,6-; 3,6-; 3,7-; 3,4-; 2,7-; 5,8-; or 6,7-position when m is the integer 2 and R is methyl. When the side chain is attached to the 2-position of the naphthalene nucleus, it is preferred that the group R is attached at the 1-, 3-, 5- or 6-position when m is the integer 1, or at the 1,4-; 1,6-; 3,7-; 5,8-; 6,7-; 3,6-; 4,5- or 6,8-position when m is the integer 2 and R is methyl.

In practice of the above described methods of the present invention a therapeutically effective amount of the compound of formula (I) or a pharmaceutical composition containing the same is administered via any of the usual and acceptable methods known in the art, either singly or in combination with another compound or compounds of the present invention or other pharmaceutical agents. These compounds or compositions can thus be administered orally or parenterally (i.e. intramuscularly, subcutaneously and intraveneously), either in the form of solid or liquid dosages including tablets, solutions, suspensions, and the like, as discussed in more detail hereinbelow. Oral administration is preferred.

The administration can be conducted in a single unit dosage form with continuous therapy or in single dosage therapy ad libitum. The method of the present invention may be practiced when relief of symptoms is specifically required, i.e. therapeutically, or as continuous or prophylactic treatment.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount for anticonvulsant use ranges from about 0.1 to about 300 mg./kg. body weight per day and preferably from about 1 to about 100 mg./kg. body weight per day. In alternate terms, for an average adult human subject, a therapeutically effective amount in accordance herewith would be, in preferred embodiments, from about 70 mg. to about 7 g. per day per subject. A therapeutically effective amount for inhibition of gastric secretion ranges from about 0.1 to about 300 mg./kg. body weight per day and preferably from about 0.25 to about 100 mg./kg. body weight per day. In alternate terms, for an average adult human subject, a therapeutically effective amount in accordance herewith would be, in preferred embodiments from about 18 mg. to about 7 g. per day per subject.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Suitable pharmaceutical carriers and their formulations are described in "Remington's Pharmaceutical Sciences" by E. W. Martin. Such compositions will, in any event, contain a therapeutically effective amount of the active compound together with a suitable amount of carrier so as to prepare the proper dosage form for proper administration to the subject.

Compounds similar to those of formula (I) have been previously described in applicant's copending applications Ser. No. 796,624, filed May 13, 1977 now abandoned and Ser. No. 848,548, filed Nov. 4, 1977 now U.S. Pat. No. 4,150,153, issued Apr. 17, 1979. The disclosures in said copending applications are incorporated by reference herein.

The compounds of the present invention may be prepared according to methods well known in the art. For example, compounds of formula (I)d wherein Z is carbonyl may be prepared in a manner analogous to that described in U.S. Pat. No. 3,717,655 to Godefroi et al. This method comprises reacting a halomethyl naphthyl ketone with imidazole in an inert organic solvent. The starting halomethyl naphthyl ketones are known or may be prepared by halogenation of the corresponding methyl naphthyl ketone by known means, for example, utilizing cupric bromide. The preparation of ketones of formula (I)d by the above described method may be carried out in an inert organic solvent, for example, dimethylformamide at a temperature between about $-10°$ and $+80°$ C.

Since not all possible combinations of substituted acetylnaphthalenes are known in the literature, the present invention is necessarily limited to those substitution patterns which are preparable by application of known methods.

Preparation of compounds of formula (I)a wherein Z is hydroxymethylene may be accomplished by the reduction of the corresponding ketone or acid addition salt thereof under standard conditions, for example, by the use of sodium tetrahydroborate in a protic solvent, for example, methanol, at a temperature between about $-20°$ and $+20°$ C.

Compounds of formula (I)b wherein Z is esterified hydroxymethylene may be prepared under usual esterification conditions from the corresponding alcohol by treatment of the alcohol with the desired acid halide or anhydride preferably in the presence of a base, preferably a tertiary amine such as pyridine or triethylamine, at a temperature between about $0°$ and $+40°$ C. in a solvent such as pyridine, tetrahydrofuran, dichloromethane, chloroform, and the like.

Compounds of formula (I)c wherein Z is $C_1$ to $C_6$ alkoxymethylene and R and m are as defined above, may be prepared from the corresponding alcohol by alkylation with Alk-X where X is a leaving group e.g. a halide, especially bromide or iodide, or a reactive ester such as a sulfonate ester, e.g. methanesulfonate or p-toluenesulfonate and Alk is as previously defined. In this method the alcohol is first converted to a metal salt, preferably an alkali metal salt, e.g. the sodium salt, and contacted with Alk-X in an inert organic solvent such as hexamethylphosphoramide, dimethylformamide or tetrahydrofuran at a temperature between about $-20°$ and $80°$ C., preferably between $0°$ and $55°$ C.

Compounds of formula (I)c wherein Z is alkylthiomethylene may be prepared in a two step procedure starting from the corresponding alcohol. In this procedure the alcohol is first converted to a leaving group such as a halide (e.g. chloride or bromide) or a reactive ester such as a sulfonate ester (e.g., a methanesulfonate and p-toluenesulfonate ester) by conventional means well known in the art before conversion to the thioether. Preparation of the thioether is accomplished by reaction of the intermediate halide or reactive ester with an alkylthiol optionally in the presence of base or preferably with a salt of the thiol, preferably an alkali metal salt e.g. the sodium salt in an inert solvent such as tetrahydrofuran, methanol at a temperature of $0°$ to $67°$ C.

Certain compounds of formula (I)e wherein Z is ketal-protected carbonyl may be prepared by treatment of the corresponding ketone (or an acid addition salt thereof) with the desired dihydric alcohol in the presence of a strong acid, for example a sulfonic acid such as p-toluenesulfonic acid or a Lewis acid such as boron trifluoride. Water is preferably removed as an azeotrope with the solvent, for example an aromatic hydrocarbon such as benzene or toluene, at a temperature sufficient to effect such azeotropic removal, e.g. from about $75°$ to about $150°$ C.

Compounds of formula (I)e wherein Z is thioketal-protected carbonyl may be prepared by treatment of the corresponding ketone (or an acid addition salt thereof) with the desired thiol or dithiol, optionally in the presence of a mineral acid such as hydrochloric acid, an organic sulfonic acid such as methanesulfonic acid or a salt, of imidazole in a polar aprotic solvent such as dimethylformamide, dimethylsulfoxide or tetrahydrofuran at a temperature between about 20° and 130° C.

Compounds of formula (I)a wherein Z is hydroxymethylene may also be prepared according to the following reaction sequence:

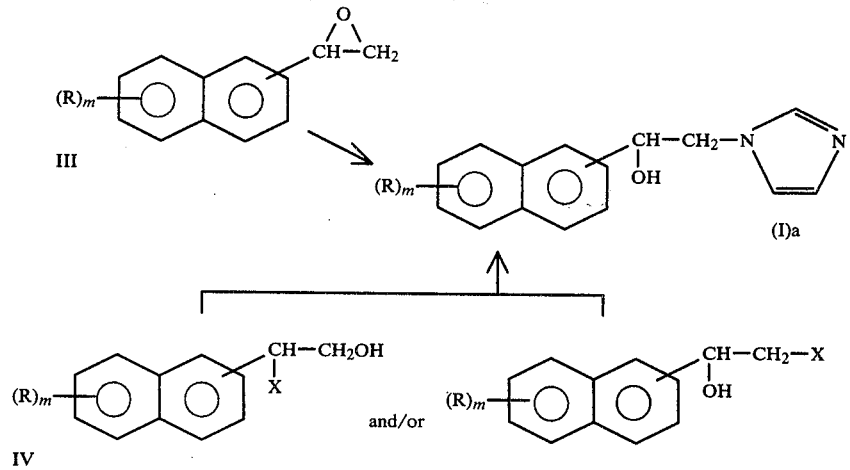

Lewis acid such as boron trifluoride or zinc chloride at a temperature between about 0° and 100° C., preferably between about 0° and 25° C.

Compounds of formula (I)e wherein Z is hemithioketal-protected carbonyl may be prepared by treatment of the corresponding ketone with the desired mercaptoalkanol under conditions similar to those described above for ketal formation.

Compounds of formula (I)e wherein Z is ketal-protected carbonyl may also be prepared according to the following reaction sequence:

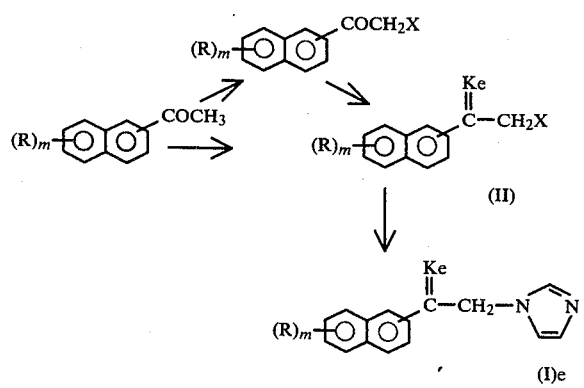

wherein X is halo (especially chloro or bromo) and m and R are as previously defined, as disclosed in U.S. Pat. Nos. 3,793,453 and 3,575,999, in the corresponding phenyl series. In this sequence the naphthyl methyl ketone is either first halogenated to the naphthyl halomethyl ketone, followed by ketalization or both steps are performed concurrently. Ketalization to form cyclic ketals may be performed essentially as described above. Ketalization to form acyclic ketals may be performed by employing an orthoester (e.g. methyl orthoformate or ethyl orthoformate) in the presence of an organic, inorganic or Lewis acid, e.g. boron trifluoride, p-toluenesulfonic acid, perchloric acid, fuming sulfuric acid, and the like. The haloketal (II) is then converted to (I)e by treatment with an alkali metal salt, e.g. the sodium wherein the epoxide (III) or the halohydrin (IV) is treated with imidazole and/or an alkali metal salt (preferably the sodium salt) thereof in a polar aprotic solvent such as dimethylformamide, dimethylsulfoxide or tetrahydrofuran at a temperature between about 0° and 100° C. Treatment of the epoxide requires one mole of imidazole in the presence of 0.05 to 1 mole of imidazole salt.

Treatment of the halohydrin requires slightly over one mole of imidazole salt, since the halohydrin is first converted in situ to the epoxide.

The subject compounds of formula (I) can be isolated as free bases; however, since many of the compounds in base form are oils and gums and/or not water soluble it is often more convenient to isolate and further characterize such compounds as acid addition salts. These salts are prepared in the usual manner, i.e., by reaction of the free base with a suitable inorganic or organic acid. If desired, the salt can be readily converted to the free base by treatment with a base such as potassium or sodium carbonate or potassium or sodium hydroxide.

As used in the specification and appended claims, unless specified to the contrary, the following terms have the meanings indicated. The term "$C_1$ to $C_6$ alkyl" is intended to mean a straight or branched chain monovalent substituent consisting of solely carbon and hydrogen containing no unsaturation and having from 1 to 6 carbon atoms. Examples of such alkyl groups include methyl, ethyl, i-propyl, n-hexyl and the like. The term "$C_1$ to $C_6$ alkoxy" refers to the above alkyl groups linked through an ether linkage and having the free valence from the oxygen. Examples of such alkoxy groups include methoxy, ethoxy, i-propoxy, hexyloxy and the like. The term "halo" refers to the groups fluoro, chloro, bromo or their corresponding halides.

The term "esterified hydroxymethylene" refers to a hydroxymethylene group which has been esterified with an alkanoic acid having from 1 to 6 carbon atoms preferably 1 to 4 carbon atoms or with benzoic acid optionally substituted with one to three substituents independently selected from $C_1$ to $C_6$ alkyl, $C_1$ to $C_6$ alkoxy and halo, preferably benzoic acid. Typical alkanoic acids include formic acid, acetic acid, propionic acid, butyric acid, isobutyric acid, valeric acid, isovaleric acid, caproic acid, and the like. The term "alkoxymethylene" refers to a hydroxymethylene group alkylated on the oxygen with a $C_1$ to $C_6$ preferably $C_1$ to $C_4$ alkyl group. The term "alkylthiomethylene" refers to a mercapto-methylene group alkylated on sulfur with a $C_1$ to $C_6$ preferably a $C_1$ to $C_4$ alkyl group. The term "ketal-protected carbonyl" refers to (i) a carbonyl group protected as an acyclic ketal derived from a monohydric straight chain alkanol having from 1 to 4 carbon atoms such as, for example, the dimethyl-, diethyl-, di(n-propyl)- and di(n-butyl) ketals and (ii) a carbonyl group protected as a cyclic ketal derived from a dihydric alcohol having 2 or 3 carbon atoms which may optionally be substituted by one or more methyl groups, for example the ethylenedioxy-, 1,3-propylenedioxy-, 1,2-propylenedioxy-, 2,2-dimethyl-1,3-propylenedioxy, 1-methyl-1,3-propylenedioxy, 1,3-dimethyl-1,3-propylenedioxy- and 2,3-butylenedioxyketals. The term "thioketal-protected carbonyl" is intended to mean (i) a carbonyl group protected as an acyclic thioketal derived from a straight or branched chain alkylthiol having from 1 to 4 carbon atoms, such as the bis(methylthio)-, bis(ethylthio)-, bis(n-propylthio)-, bis(isopropylthio)- and bis(isobutylthio)-ketals, or from thiophenol or benzyl mercaptan (i.e. the bis(phenylthio)- and bis(benzylthio)- ketals), and (ii) a carbonyl group protected as a cyclic thioketal derived from an alkylenedithiol having 2 or 3 carbon atoms which may optionally be substituted by one or more methyl groups, for example, the ethylenedithio-, 1,3-propylenedithio- and 2,2-dimethyl-1,3-propylene- dithioketals. The term "hemithioketal-protected carbonyl" shall mean a carbonyl group protected as a cyclic hemithioketal derived from 2-mercaptoethanol or 3-mercapto-1-propanol. The term "pharmaceutically acceptable acid addition salts" refers to salts of the free bases of formula (I), which salts possess the desired pharmacological activity and which are neither biologically nor otherwise undesirable. Such salts may be formed with inorganic acids such as hydrochloric acid, hydrobromic acid, sulfuric acid, nitric acid or phosphoric acid; or with organic acids such as acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

Compounds of formula (I) wherein Z is hydroxymethylene, esterified hydroxymethylene, alkoxymethylene, alkylthiomethylene or hemithioketal protected carbonyl possess a chiral center. Accordingly, these compounds may be prepared in either optically active form, or as a racemic mixture. Unless otherwise specified, the compounds described herein are all in the racemic form. However, the scope of the subject invention is not to be limited to the racemic form but is to encompass the individual optical isomers of the subject compounds.

If desired, compounds of formula (I) wherein Z is hydroxymethylene, esterified hydroxymethylene, alkoxymethylene, alkylthiomethylene or hemithioketal protected carbonyl may be prepared in optically active form by conventional resolution means known per se, for example, by the separation (e.g., fractional crystallization) of the diastereomeric salts formed by reaction of, e.g., racemic compounds of formula (I) wherein Z is hydroxymethylene, esterified hydroxymethylene, alkoxymethylene, alkylthiomethylene or hemithioketal protected carbonyl with an optically active acid or by separation of the diastereomeric esters formed by reaction of such a racemic alcohol wherein Z is hydroxymethylene with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acid, and the like. The separated pure diasteromeric salts or esters may then be cleaved by standard means to afford the respective optical isomers of the desired compound.

The following specific description is given to enable those skilled in the art to more clearly understand and practice the present invention. It should not be considered as a limitation upon the scope of the invention but merely as illustrative and representative thereof.

Preparation 1

Methyl 2-(6,7-dimethylnaphthyl) ketone (1.32 g.), in 40 ml of a 1:1 mixture of chloroform and ethyl acetate is treated with 2.97 g. of copper (II) bromide. The resulting reaction mixture is heated under reflux with vigorous stirring overnight, the solvent is removed, ether added and the copper (I) bromide removed by filtration. Evaporation of the filtrate under reduced pressure yields crude bromomethyl 2-(6,7-dimethylnaphthyl) ketone, used directly in the next step.

Preparation 2

Chloroacetyl chloride (15.9 ml) is added to a mixture of 26.67 g of anhydrous aluminum chloride in 35 ml of nitrobenzene at 0° followed by the dropwise addition with stirring of 31.25 g of 2-ethylnaphthalene over 15 minutes. After stirring overnight at room temperature the mixture is poured on to a mixture of 500 g of ice and 100 ml concentrated hydrochloric acid. This is then extracted with ethyl acetate, the extracts washed with aqueous potassium carbonate, dried ($MgSO_4$) and evaporated. After distillation of the nitrobenzene, the mixture is distilled as a yellow oil at 177° (0.4 mm). The resulting mixture of isomers is chromatographed on silica gel eluting with toluene to give 8.75 g of pure 1-chloroacetyl-7-ethylnaphthalene as an oil; and 6.3 g of 2-chloroacetyl-6-ethylnaphthalene as a colorless solid, recrystallized from hexane with mp 75°–76.5° C.

Preparation 3

A mixture of 20 g. of anhydrous aluminum chloride and 30 ml nitrobenzene is treated at room temperature with 8.3 ml of chloroacetyl chloride and warmed to dissolve solids. At room temperature, 25.54 g of a mixture of isopropylnaphthalene isomers is added dropwise and the mixture stirred for four hours and worked up as in Preparation 1. The resulting crude dark oil is distilled at 185° (0.19 mm) to give 22 g of an amber oil containing at least four products. The mixture is chromatographed on silica gel eluting with 25% toluene/hexane to give pure 1-chloroacetyl-4-isopropylnaphthalene as an oil.

Example 1

To a stirred, ice-cooled solution of 7.07 g. of imidazole in 15 ml. of dimethylformamide is added 5.5 g. of chloromethyl 1-(7-methylnaphthyl) ketone in 10 ml dimethylformamide. The mixture is stirred at room temperature overnight and for 2 hours at 80° C. The solution is poured into water, the product extracted with ether and the extracts washed with water and dried (MgSO4). The product is converted to its hydrobromide acid addition salt by addition of ethereal hydrogen bromide until precipitation is complete. The resulting solid is recrystallized from acetone to yield colorless crystals of 1-[(7-ethyl-1-naphthoyl)methyl]imidazole hydrobromide, m.p. 187.5°–190.5° C.

Repeating the procedure of Example 1, utilizing the appropriately substituted-naphthyl bromo(chloro)methyl ketone there may be prepared:

1-[(6-bromo-2-naphthoyl)methyl]imidazole hydrochloride, m.p. 283.5°–287° C.;
1-[(6-chloro-2-naphthoyl)methyl]imidazole hydrochloride, m.p. 277°–279° C.;
1-[(6-fluoro-2-naphthoyl)methyl]imidazole;
1-[(6-methyl-2-naphthoyl)methyl]imidazole hydrochloride, m.p. 271°–272° C. (d);
1-[(1-methyl-2-naphthoyl)methyl]imidazole;
1-[(3-methyl-2-naphthoyl)methyl]imidazole;
1-[(5-methyl-2-naphthoyl)methyl]imidazole;
1-[(6-ethyl-2-naphthoyl)methyl]imidazole hydrobromide, m.p. 263.5°–264° C.;
1-[(6-i-propyl-2-naphthoyl)methyl]imidazole;
1-[(6-t-butyl-2-naphthoyl)methyl]imidazole;
1-[(6,7-dimethyl-2-naphthoyl)methyl]imidazole hydrochloride, m.p. 239.5°–242° C. (d);
1-[(1,4-dimethyl-2-naphthoyl)methyl]imidazole;
1-[(1,6-dimethyl-2-naphthoyl)methyl]imidazole;
1-[(3,7-dimethyl-2-naphthoyl)methyl]imidazole;
1-[(5,8-dimethyl-2-naphthoyl)methyl]imidazole;
1-[(3,6-dimethyl-2-naphthoyl)methyl]imidazole;
1-[(6,8-dimethyl-2-naphthoyl)methyl]imidazole;
1-[(4,5-dimethyl-2-naphthoyl)methyl]imidazole;
1-[(1-methoxy-2-naphthoyl)methyl]imidazole hydrochloride, m.p. 170°–172.5° C.;
1-[(6-methoxy-2-naphthoyl)methyl]imidazole hydrochloride, m.p. 233°–237.5° C. (d);
1-[(6-ethoxy-2-naphthoyl)methyl]imidazole;
1-[(6-hydroxy-2-naphthoyl)methyl]imidazole hydrochloride, m.p. 264°–268° C.;
1-[(1-hydroxy-2-naphthoyl)methyl]imidazole;
1-[(7-bromo-1-naphthoyl)methyl]imidazole;
1-[(3-bromo-1-naphthoyl)methyl]imidazole;
1-[(7-methyl-1-naphthoyl)methyl]imidazole hydrochloride, m.p. 241.5°–244° C.;
1-[(4-methyl-1-naphthoyl)methyl]imidazole;
1-[(7-ethyl-1-naphthoyl)methyl]imidazole hydrochloride;
1-[(7-ethyl-1-naphthoyl)methyl]imidazole hydrobromide, m.p. 187.5°–190.5° C.;
1-[(4-ethyl-1-naphthoyl)methyl]imidazole;
1-[(4-i-propyl-1-naphthoyl)methyl]imidazole hydrochloride, m.p. 199.5°–203° C.;
1-[(6,7-dimethyl-1-naphthoyl)methyl]imidazole hydrochloride, m.p. 271°–274° C. (d);
1-[(6,7-dimethoxy-1-naphthoyl)methyl]imidazole hydrochloride, m.p. 267.5°–270° C.;
1-[(2,3-dimethyl-1-naphthoyl)methyl]imidazole;
1-[(2,6-dimethyl-1-naphthoyl)methyl]imidazole;
1-[(3,6-dimethyl-1-naphthoyl)methyl]imidazole; and
1-[(3,4-diethyl-1-naphthoyl)methyl]imidazole.

EXAMPLE 2

To 2.1 g. of the above obtained 1-[(7-ethyl-1-naphthoyl)methyl]imidazole hydrobromide in 50 ml. of methanol at 0°–5° C. is added, with stirring, excess sodium tetrahydroborate. After stirring for 30 minutes at 0° C., the reaction mixture is evaporated to dryness. The resultant residue is treated with water and the product which crystallizes is filtered off, washed with water and recrystallized from ethyl acetate to yield 1-[2-hydroxy-2-(7-ethyl-1-naphthyl)ethyl]imidazole.

Similarly there may be prepared the following:

1-[2-hydroxy-2-(6-methyl-2-naphthyl)ethyl]imidazole;
1-[2-hydroxy-2-(6-ethyl-2-naphthyl)ethyl]imidazole;
1-[2-hydroxy-2-(6-n-propyl-2-naphthyl)ethyl]imidazole;
1-[2-hydroxy-2-(6-i-propyl-2-naphthyl)ethyl]imidazole;
1-[2-hydroxy-2-(6-t-butyl-2-naphthyl)ethyl]imidazole;
1-[2-hydroxy-2-(6-chloro-2-naphthyl)ethyl]imidazole;
1-[2-hydroxy-2-(6-bromo-2-naphthyl)ethyl]imidazole;
1-[2-hydroxy-2-(4-methyl-1-naphthyl)ethyl]imidazole;
1-[2-hydroxy-2-(4-ethyl-1-naphthyl)ethyl]imidazole;
1-[2-hydroxy-2-(4-i-propyl-1-naphthyl)ethyl]imidazole;
1-[2-hydroxy-2-(7-methyl-1-naphthyl)ethyl]imidazole; and
1-[2-hydroxy-2-(7-ethyl-1-naphthyl)ethyl]imidazole.

EXAMPLE 3

A mixture of 0.7 g. of 1-[(6-ethyl-2-naphthoyl)methyl]imidazole, 4 ml of ethylene glycol and 1.3 g. of anhydrous p-toluenesulfonic acid in 50 ml. of toluene is heated overnight under reflux through a Dean-Stark trap. The trap is the replaced by a separatory funnel containing 4 A molecular sieves and heating is continued for a further day. After cooling, the mixture is treated with 100 ml. of ethyl acetate, neutralized by pouring into excess aqueous potassium carbonate and the organic phase separated, washed with water, dried (MgSO4) and evaporated to afford 1-[2,2-ethylenedioxy-2-(6-ethyl-2-naphthyl)ethyl]imidazole. This is purified by chromatography on silica gel eluting with 10% methanol/dichloromethane and the hydrochloride salt prepared by dropwise addition of ethereal hydrogen chloride until precipitation is complete. Filtration and recrystallization from acetone/methanol gives 0.38 g. pure hydrochloride, m.p. 251° C.

Repeating the procedure above utilizing the appropriate starting materials there may be prepared:

1-[2,2-(1,3-propylenedioxy)-2-(6-methyl-2-naphthyl)ethyl]imidazole;
1-[2,2-(2,2-dimethyl-1,3-propylenedioxy)-2-(6-methyl-2-naphthyl)ethyl]imidazole;
1-[2,2-(1-methyl-1,3-propylenedioxy)-2-(6-chloro-2-naphthyl)ethyl]imidazole;
1-[2,2-ethylenedioxy-2-(7-ethyl-1-naphthyl)ethyl]imidazole;
1-[2,2-(1,3-propylenedioxy)-2-(7-ethyl-1-naphthyl)ethyl]imidazole;
1-[2,2-ethylenedioxy-2-(4-isopropyl-1-naphthyl)ethyl]imidazole;
1-[2,2-(1,2-propylenedioxy)-2-(6-methyl-2-naphthyl)ethyl]imidazole;
1-[2,2-ethylenedioxy-2-(7-methyl-1-naphthyl)ethyl]imidazole;
1-[2,2-(2,3-butylenedioxy)-2-(6,7-dimethyl-2-naphthyl)ethyl]imidazole;
1-[2,2-ethylenedioxy-2-(6-methyl-2-naphthyl)ethyl]imidazole;
1-[2,2-ethylenedioxy-2-(4-methyl-1-naphthyl)ethyl]imidazole; and
1-[2,2-ethylenedioxy-2-(4-ethyl-1-naphthyl)ethyl]imidazole.

EXAMPLE 4

A solution of 1.00 g. of 1-[(6-bromo-2-naphthoyl)methyl]imidazole hydrochloride in 6 ml. of 98% methanesulfonic acid is treated at room temperature with 4 ml. of ethyl mercaptan and the mixture stirred overnight under nitrogen. The resulting solution is added to excess aqueous potassium carbonate, the product extracted with ethyl acetate and the extracts washed, dried (MgSO₄) and evaporated. The residue was chromatographed on silica gel eluting with 5% acetone in dichloromethane and the resulting pure 1-[2,2-bis(ethylthio)-2-(6-bromo-2-naphthyl)ethyl]imidazole dissolved in ether. Dropwise addition of ethereal hydrogen chloride precipitates 0.62 g. of the hydrochloride which is recrystallized from ethyl acetate/methanol to give 0.46 g. pure product, m.p. 216°–217.5° C.

Repeating the procedure above utilizing the appropriate starting materials there may be prepared:
1-[2,2-bis(methylthio)-2-(6-ethyl-2-naphthyl)ethyl]imidazole;
1-[2,2-bis(ethylthio)-2-(6-ethyl-2-naphthyl)ethyl]imidazole-hydrochloride salt, m.p. 130° C.;
1-[2,2-bis(n-propylthio)-2-(6-bromo-2-naphthyl)ethyl]imidazole-hydrochloride salt, m.p. 183.5°–184.5° C.;
1-[2,2-bis(isobutylthio)-2-(6-methoxy-2-naphthyl)ethyl]imidazole;
1-[2,2-ethylenedithio-2-(6-methyl-2-naphthyl)ethyl]imidazole;
1-[2,2-(1,3-propylenedithio)-2-(6-methyl-2-naphthyl)ethyl]imidazole;
1-[2,2-bis(ethylthio)-2-(6,7-dimethyl-2-naphthyl)ethyl]imidazole-hydrochloride salt, m.p. 195°–198° C.;
1-[2,2-bis(isopropylthio)-2-(4-methyl-1-naphthyl)ethyl]imidazole;
1-[2,2-ethylenedithio-2-(4-ethyl-1-naphthyl)ethyl]imidazole;
1-[2,2-bis(ethylthio)-2-(7-methyl-1-naphthyl)ethyl]imidazole;
1-[2,2-bis(n-propylthio)-2-(6,7-dimethyl-2-naphthyl)ethyl]imidazole-hydrochloride salt, m.p. 140°–145,5° C.;
1-[2,2-bis(n-butylthio)-2-(2-methoxy-1-naphthyl)ethyl]imidazole;
1-[2,2-bis(phenylthio)-2-(6-hydroxy-2-naphthyl)ethyl]imidazole; and
1-[2,2-bis(benzylthio)-2-(6-methoxy-2-naphthyl)ethyl]imidazole.

EXAMPLE 5

A solution of 1.26 g. 1-[2-hydroxy-2-(6-methyl-2-naphthyl)ethyl]imidazole in 20 ml. pyridine is treated dropwise with stirring with 0.72 ml. of benzoyl chloride and the mixture stirred overnight. The resulting solution is poured into 100 ml. water, extracted with ethyl acetate and the extracts washed, dried (MgSO₄) and evaporated in vacuo to remove residual pyridine and afford 1-[2-benzoyloxy-2-(6-methyl-2-naphthyl)ethyl]imidazole. The residue is dissolved in ether, treated with ethereal hydrogen chloride and the resulting precipitate recrystallized from acetone/methanol to give the hydrochloride salt.

EXAMPLE 6

To a solution of 2.38 g. of 1-[2-(6-methyl-2-naphthyl)-2-hydroxyethyl]imidazole in 40 ml. of hexamethylphosphoramide under nitrogen is added 480 mg. of a 56% dispersion of sodium hydride in mineral oil. After stirring for 1 hour at room temperature, the temperature is adjusted to 50° C. and stirring is continued for 1 to 2 hours. The reaction mixture is then cooled to about 5° C. and 0.74 ml. of iodomethane is added dropwise. Thereafter, the solution is stirred at 5° to 10° C. for 1 hour, at room temperature for 4 hours and then heated at 50° C. for 2 hours. The reaction mixture is then poured into water and the resultant aqueous mixture extracted with ether and the ether extracts washed with water. The organic phase is dried over magnesium sulfate and evaporated. The resulting residue may be chromatographed on silica gel to effect purification of the free base. Elution of the gel with 5 to 10% methanol in dichloromethane yields 1-[2-(6-methyl-2-naphthyl)-2-(methoxy)ethyl]imidazole.

The hydrochloride salt of the free base is prepared by the dropwise addition of ethereal hydrogen chloride to the free base in ether. When precipitation is complete the salt is collected by filtration and recrystallized from ethyl acetate/methanol to yield 1-[2-(6-methyl-2-naphthyl)-2-(methoxy)ethyl]imidazole hydrochloride.

Repeating the above procedure using the appropriate starting materials there may be prepared:
1-[2-(6-ethyl-2-naphthyl)-2-(methoxy)ethyl]imidazole;
1-[2-(6-methyl-2-naphthyl)-2-(ethoxy)ethyl]imidazole;
1-[2-(4-methyl-1-naphthyl)-2-(methoxy)ethyl]imidazole;
1-[2-(4-ethyl-1-naphthyl)-2-(methoxy)ethyl]imidazole;
1-[2-(4-isopropyl-1-naphthyl)-2-(methoxy)ethyl]imidazole;
1-[2-(7-methyl-1-naphthyl)-2-(methoxy)ethyl]imidazole; and
1-[2-(7-ethyl-1-naphthyl)-2-(methoxy)ethyl]imidazole.

EXAMPLE 7

Thionyl chloride (5 ml.) and 2.0 g. of 1-[2-(6-methyl-2-naphthyl)-2-hydroxyethyl]imidazole are stirred at room temperature for about 20 minutes. Thereafter, the solution is evaporated to dryness and the residue is treated with ethyl acetate and filtered to yield 1-[2-(6-methyl-2-naphthyl)-2-chloroethyl]imidazole hydrochloride.

The above obtained chloride, i.e., 1-[2-(6-methyl-2-naphthyl)-2-chloroethyl]imidazole hydrochloride (1.0 g.) is added to the salt prepared in situ from 0.78 g. of n-propyl mercaptan and 380 mg. of sodium hydride (56% dispersion in mineral oil) in 50 ml. of dry tetrahydrofuran. The mixture is stirred for 4 hours at 25° C. and then evaporated to dryness. The residue is extracted with ether and the ether extracts washed with water, dried over magnesium sulfate and evaporated. The resulting residue may be chromatographed on silica gel to effect purification of the free base. Elution of the gel with 5 to 10% acetone in dichloromethane yields 1-[2-(6-methyl-2-naphthyl)-2-(n-propylthio)ethyl]imidazole.

The nitrate salt of the free base is prepared by the dropwise addition of concentrated nitric acid (d=1.42) to the free base in ether. When precipitation is complete the product is collected by filtration and recrystallized from ethyl acetate to yield 1-[2-(6-methyl-2-naphthyl)-2-(n-propylthio)ethyl]imidazole nitrate.

Repeating the above procedure using the appropriate starting materials there may be prepared:
1-[2-(6-methyl-2-naphthyl)-2-(methylthio)ethyl]imidazole;
1-[2-(6-ethyl-2-naphthyl)-2-(methylthio)ethyl]imidazole;

1-[2-(7-methyl-1-naphthyl)-2-methylthio)ethyl-
   ]imidazole;
1-[2-(7-ethyl-1-naphthyl)-2-methylthio)ethyl]imidazole;
1-[2-(4-methyl-1-naphthyl)-2-methylthio)ethyl-
   ]imidazole;
1-[2-(4-ethyl-1-naphthyl)-2-methylthio)ethyl]imidazole;
   and
1-[2-(4-isopropyl-1-naphthyl)-2-methylthio)ethyl-
   ]imidazole.

EXAMPLE 8

Repeating the procedure of Example 5, utilizing the appropriate starting material, there may be prepared the following compounds:
1-[2-acetoxy-2-(6-ethyl-2-naphthyl)ethyl]imidazole;
1-[2-propionyloxy-2-(6-methyl-2-naphthyl)ethyl-
   ]imidazole;
1-[2-butyryloxy-2-(6-methyl-2-naphthyl)ethyl-
   ]imidazole;
1-[2-isobutyryloxy-2-(6-chloro-2-naphthyl)ethyl-
   ]imidazole;
1-[2-hexanoyloxy-2-(6-methoxy-2-naphthyl)ethyl-
   ]imidazole;
1-[2-acetoxy-2-(4-ethyl-1-naphthyl)ethyl]imidazole;
1-[2-propionyloxy-2-(4-methyl-1-naphthyl)ethyl-
   ]imidazole;
1-[2-butyryloxy-2-(7-methyl-1-naphthyl)ethyl-
   ]imidazole;
1-[2-isobutyryloxy-2-(7-ethyl-1-naphthyl)ethyl-
   ]imidazole;
1-[2-hexanoyloxy-2-(2-methoxy-1-naphthyl)ethyl-
   ]imidazole; and
1-[2-benzoyloxy-2-(2-methoxy-1-naphthyl)ethyl-
   ]imidazole.

EXAMPLE 9

A solution of 2.63 g. of bromomethyl 2-(6-methylnaphthyl) ketone, 1.7 g. trimethyl orthoformate and a few crystals of p-toluenesulfonic acid (anhydrous) in 20 ml. anhydrous methanol is heated under reflux for two hours. After cooling to room temperature, two drops of phenolphthalein solution are added and a solution of sodium methoxide in methanol is added dropwise until a pink color persists. After removal of the solvent under reduced pressure the resulting oil is dissolved in ether, decolorized with charcoal and the ether removed to give 3.11 g. (100%) of bromomethyl 2-(6-methylnaphthyl)ketone dimethyl ketal as a colorless oil.

Sodium hydride (0.40 g. of 50% dispersion in mineral oil) is added to 0.61 g. imidazole in 10 ml dimethylformamide and the mixture stirred at room temperature until the evolution of hydrogen is complete. Bromomethyl 2-(6-methylnaphthyl)ketone dimethyl ketal (2.31 g.) in 5 ml dimethylformamide is then added and the mixture stirred for 24 hours at 110° under nitrogen. The resulting solution is poured into water (400 ml.), extracted with ether (400 ml. total), and the extracts washed, dried (MgSO4) and evaporated. The resulting crude solid (2.3 g.) is recrystallized from toluene to give 1-[2-(6-methyl-2-naphthyl)-2,2-dimethoxyethyl]imidazole as a colorless solid.

EXAMPLE 10

1-[(6-Ethyl-2-naphthoyl)methyl]imidazole hydrochloride (600 mg.) and p-toluenesulfonic acid monohydrate (570 mg.) in toluene (10 ml.) containing a little benzene are treated with 2-mercaptoethanol (4 ml.). A pressure-equalized addition funnel filled with activated 4 A molecular sieves in toluene is placed above the flask as a modified Dean-Stark trap and the mixture heated under reflux with stirring for 18 hours. The resulting mixture is then added with stirring to excess aqueous potassium carbonate, the product extracted with ether (with filtration) and the extracts washed, dried (MgSO4) and evaporated. Purification by chromatography on silica gel eluting with ethyl acetate gives pure 1-[(6-ethyl-2-naphthoyl)methyl]imidazole ethylene hemithioketal.

EXAMPLE 11

Ethereal hydrogen chloride is added dropwise to a solution of 1.0 g. 1-[(6-methyl-2-naphthoyl)methyl)imidazole in 100 ml. ether until precipitation is complete. The product is filtered, washed with ether, air dried and recrystallized from methanol/acetone to yield 1-[(6-methyl-2-naphthoyl)methyl]imidazole hydrochloride, m.p. 271°-272° C. (decomp).

In a similar manner, all compounds of formula (I) in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 12

1-[(6-Methyl-2-naphthoyl)methyl]imidazole hydrochloride (1.0 g.) suspended in 50 ml. of ether is stirred with excess dilute aqueous potassium carbonate solution until the salt is completely dissolved. The organic layer is then separated, washed twice with water, dried over magnesium sulfate and evaporated to yield 1-[(6-methyl-2-naphthoyl)methyl]imidazole.

In a similar manner the acid addition salts of all compounds of formula (I) may be converted to the corresponding compounds in free base form.

EXAMPLE 13

The following illustrates a pharmaceutical composition for oral administration which may be prepared for the compounds of the present invention, e.g. 1-[(7-ethyl-1-naphthoyl)methyl]imidazole hydrobromide,

|  | parts by weight |
| --- | --- |
| Active compound | 200 |
| Magnesium stearate | 3 |
| Starch | 30 |
| Lactose | 116 |
| Polyvinylpyrrolidone | 3 |

The above ingredients are combined and granulated using methanol as the solvent. The formulation is then dried and formed into tablets (containing 200 mg. of active compound each) with an appropriate tabletting machine.

While the present invention has been described with reference to specific embodiments thereof, it should be understood by those skilled in the art that various changes may be made and equivalents may be substituted without departing from the true spirit and scope of the invention. In addition, many modifications can be

What is claimed is:

1. A compound of the formula

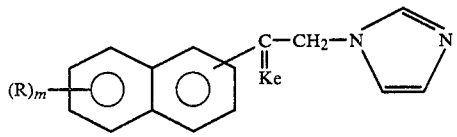

wherein m is an integer of 1, 2 or 3; R is independently selected from the group $C_1$ to $C_6$ alkyl, $C_1$ to $C_6$ alkoxy, halo, trifluoromethyl and hydroxy; Ke is selected from the group (i) a carbonyl group protected as an acyclic ketal derived from a monohydric straight chain alkanol having from one to four carbon atoms, (ii) a carbonyl group protected as a cyclic ketal wherein the cyclic ketal is selected from the group consisting of ethylenedioxy, 1,3-propylenedioxy, 1,2-propylenedioxy, 2,2-dimethyl-1,3-propylenedioxy, 1-methyl-1,3-propylenedioxy, 1,3-dimethyl-1,3-propylenedioxy and 2,3-butylenedioxy, (iii) a carbonyl group protected as an acyclic thioketal derived from a straight or branched chain alkylthio having from one to four carbon atoms or from thiophenol or benzylmercaptan, (iv) a carbonyl group protected as a cyclic thioketal derived from an alkylene dithio having two or three carbon atoms which may optionally be substituted by one or more methyl groups, or (v) a carbonyl group protected as a cyclic hemithioketal derived from 2-mercaptoethanol or 3-mercapto-1-propanol; and the pharmaceutically acceptable acid addition salts thereof.

2. The compound of claim 1 wherein Ke is (i) a carbonyl group protected as an acyclic ketal derived from a monohydric straight chain alkanol having from one to four carbon atoms, (ii) a carbonyl group protected as a cyclic ketal wherein the cyclic ketal is selected from the group consisting of ethylenedioxy, 1,3-propylenedioxy, 1,2-propylenedioxy, 2,2-dimethyl-1,3-propylenedioxy, 1-methyl-1,3-propylenedioxy, 1,3-dimethyl-1,3-propylenedioxy and 2,3-butylenedioxy, (iii) a carbonyl group protected as an acyclic thioketal derived from a straight or branched chain alkylthio having from one to four carbon atoms or from thiophenol or benzylmercaptan, or (iv) a carbonyl group protected as a cyclic thioketal derived from an alkylene dithio having two or three carbon atoms which may optionally be substituted by one or more methyl groups, R is selected from the group $C_1$ to $C_4$ alkyl and halo; and m is the integer 1 or 2 and the pharmaceutically acceptable acid addition salts thereof.

3. The compound of claim 2 wherein Ke is (i) a carbonyl group protected as an acyclic ketal derived from a monocyclic straight chain alkanol having one to four carbon atoms or (ii) a carbonyl group protected as a cyclic ketal wherein the cyclic ketal is selected from the group consisting of ethylenedioxy, 1,3-propylenedioxy, 1,2-propylenedioxy, 2,2-dimethyl-1,3-propylenedioxy, 1-methyl-1,3-propylenedioxy, 1,3-dimethyl-1,3-propylenedioxy and 2,3-butylenedioxy, R is methyl, ethyl, chloro or bromo; and m is the integer 1 and the pharmaceutically acceptable acid addition salts thereof.

4. The compound of claim 3 that is 1-[2,2-ethylenedioxy-2-(6-ethyl-2-naphthyl)ethyl]imidazole and the pharmaceutically acceptable acid addition salts thereof.

5. A pharmaceutical composition useful for treating or preventing convulsions in a mammalian subject which comprises a therapeutically effective amount of a compound of claim 1 in admixture with a pharmaceutically acceptable, non-toxic carrier.

6. A pharmaceutical composition useful for inhibiting gastric secretion in a mammalian subject which comprises a therapeutically effective amount of a compound of claim 1 in admixture with a pharmaceutically acceptable, non-toxic carrier.

7. A method of treating or preventing convulsions in a mammalian subject which comprises administering a therapeutically effective amount of a compound of claim 1 to a mammalian subject in need of such treatment.

8. A method of inhibiting gastric secretion in a mammalian subject which comprises administering a therapeutically effective amount of a compound of claim 1 to a mammalian subject in need of such treatment.

* * * * *